United States Patent
Chok et al.

(10) Patent No.: US 10,393,912 B2
(45) Date of Patent: Aug. 27, 2019

(54) METHOD OF AND APPARATUS FOR INVERTING THREE-DIMENSIONAL FLUID PROPERTY DISTRIBUTION OVER THE (T1,T2,D)DOMAIN FROM NMR MEASUREMENTS

(71) Applicant: Weatherford Technology Holdings, LLC, Houston, TX (US)

(72) Inventors: Hamed Chok, Houston, TX (US); Endre Anderssen, Houston, TX (US)

(73) Assignee: Weatherford Technology Holdings, LLC, Houston, TX (US)

( * ) Notice: Subject to any disclaimer, the term of this patent is extended or adjusted under 35 U.S.C. 154(b) by 313 days.

(21) Appl. No.: 14/790,419

(22) Filed: Jul. 2, 2015

(65) Prior Publication Data
US 2017/0003411 A1    Jan. 5, 2017

(51) Int. Cl.
| | | |
|---|---|---|
| *G01V 3/32* | (2006.01) | |
| *G01V 3/34* | (2006.01) | |
| *G01V 3/38* | (2006.01) | |
| *G01R 33/44* | (2006.01) | |
| *G01N 24/08* | (2006.01) | |

(52) U.S. Cl.
CPC ............. *G01V 3/32* (2013.01); *G01R 33/448* (2013.01); *G01V 3/34* (2013.01); *G01V 3/38* (2013.01); *G01N 24/081* (2013.01)

(58) Field of Classification Search
CPC ... G01V 3/32; G01V 3/34; G01V 3/38; G01R 33/448; G01N 24/081
See application file for complete search history.

(56) References Cited

U.S. PATENT DOCUMENTS

| | | |
|---|---|---|
| 5,517,115 A | 5/1996 | Prammer |
| 6,255,819 B1 | 7/2001 | Day et al. |
| 6,937,014 B2 | 8/2005 | Sun et al. |
| 6,960,913 B2 | 11/2005 | Heaton |
| 7,034,528 B2 | 4/2006 | Minh et al. |
| 7,388,374 B2 | 6/2008 | Minh et al. |
| 7,538,547 B2 | 5/2009 | Heaton |

(Continued)

FOREIGN PATENT DOCUMENTS

EP    1896876 A1    3/2008

OTHER PUBLICATIONS

Coates et al. ("NMR Logging: Principals and Application," Halliburton Wireline & Perforating, 1999).*

(Continued)

*Primary Examiner* — Yasser A Abdelaziez
(74) *Attorney, Agent, or Firm* — Blank Rome, LLP

(57) ABSTRACT

A method is disclosed of inverting three dimensional fluid property distribution. The method includes comparing a detected NMR signal with a plurality of modeled signal values derived from precomputed values of NMR signal contribution values at prechosen ($T_1$, $T_2$, D) value tuples; identifying one or more modeled signals satisfying domain constraints and in respect of which an objective function involving a respective detected NMR signal and a modeled signal is optimized; selecting one or more of the solutions resulting in optimized objective; and using each selected optimized solution to characterize the one or more properties of fluid in the formation. The method also includes processing the resulting solutions as e.g. graphical or tabular data. Also disclosed is apparatus for performing the method.

37 Claims, 5 Drawing Sheets

(56) References Cited

U.S. PATENT DOCUMENTS

| | | | |
|---|---|---|---|
| 7,565,833 B2 | 7/2009 | Gillen et al. | |
| 8,044,662 B2 | 10/2011 | Fransson et al. | |
| 8,633,691 B2 | 1/2014 | Hoffman et al. | |
| 8,643,363 B2 | 2/2014 | Warntjes | |
| 8,736,263 B2 | 5/2014 | Minh | |
| 2005/0206378 A1 | 9/2005 | Hamdan et al. | |
| 2005/0270023 A1 | 12/2005 | Freedman | |
| 2008/0183390 A1 | 7/2008 | Hamdan et al. | |
| 2011/0025324 A1* | 2/2011 | Fransson | G01N 24/081 324/307 |
| 2013/0080058 A1 | 3/2013 | Wu et al. | |
| 2014/0129149 A1* | 5/2014 | Gzara | G01V 3/38 702/11 |
| 2014/0292325 A1* | 10/2014 | Heule | G01R 33/448 324/309 |
| 2015/0071514 A1* | 3/2015 | Wang | A61B 5/7221 382/131 |

OTHER PUBLICATIONS

Sun, Boqin et al.; "A Global Inversion Method for Multi-Dimensional NMR Logging"; Journal Of Magnetic Resonance; vol. 172; Issue 1; Jan. 2005; pp. 152-160.

Tan, Maojin et al.; "A New Inversion Method for (T2, D) 2D NMR Logging and Fluid"; Computers & Geosciences; vol. 51; Feb. 2013; pp. 366-380.

Office Action in counterpart Canadian Application No. 2,934,908 dated Apr. 25, 2017, 5 Pages.

Search Report in counterpart European Application No. 16275093.9-1559 dated Jan. 3, 2017, 12 Pages.

\* cited by examiner

METHOD OF AND APPARATUS FOR INVERTING THREE-DIMENSIONAL FLUID PROPERTY DISTRIBUTION OVER THE (T1,T2,D)DOMAIN FROM NMR MEASUREMENTS

BACKGROUND OF THE INVENTION

Disclosed herein generally are methods and systems for nuclear magnetic resonance (NMR) logging of subterranean formations, especially those containing fuel hydrocarbons in liquid or gaseous form; water; or brine. The invention concerns a method and apparatus for inverting three-dimensional fluid property distribution from NMR log data, especially pulsed NMR log data.

As is well known the logging of subterranean formations represents an extremely important contribution to the search for and recovery of rock-borne hydrocarbons that provide overwhelmingly the most commonly exploited sources of energy and chemicals used by mankind.

NMR logging in general has been in use for some decades. So-called "pulsed" NMR logging has been in widespread use since the 1990's.

Broadly speaking in pulsed NMR logging a cylindrical logging tool is moved (supported e.g. on wireline, the nature of which is known to the person of skill in the art; or on drill pipe, the nature of which is also known to the person of skill in the art) along a borehole formed in a fluid-bearing formation. In some NMR logging tool designs the logging tool is periodically halted in the borehole and in some other designs the logging tool is capable of logging while it is moving.

The logging tool includes one or more magnets the purpose of which is to emit a static magnetic field $B_0$ into the formation in which the logging tool is deployed. This aligns (polarizes) protons in fluid contained within pores in the formation from a random (resting) state to the direction of the imposed $B_0$ magnetic field.

It takes a certain time for the protons to become aligned in this way following the application of the static magnetic field. This time is known as the longitudinal relaxation time, denoted $T_1$. $T_1$ is sometimes called the "spin-lattice" relaxation time.

Protons that are aligned to an imposed magnetic field will precess towards the un-polarized, random state if the field is removed.

Precession of the protons gives rise to a detectable, decaying magnetic field. One or more antennae in the logging tool detect the decaying magnetic field, which is related to the $T_1$ time by a known expression. The antennae generate signals indicative of the detected magnetic field values. It is possible to calculate $T_1$ values based on the signals detected as a result of the decaying magnetic fields caused by precession of the protons.

$T_1$ is a useful quantity that may be regarded as indicating the ease with which the protons become aligned in the static magnetic field. Thus $T_1$ is in part indicative of the extent to which the protons interact with the boundaries of pores in the formation. In turn this can provide indications of the sizes of the pores. $T_1$ also can be used to derive a measure of the viscosity of fluids contained within the pores.

The logging tool also generates timed bursts (pulse sequences) of radio frequency (RF) energy that give rise to an oscillating magnetic field $B_1$. This tilts the aligned protons perpendicular to the direction of the applied magnetic field and causes them to precess in phase to one another. This phenomenon is referred to as nuclear magnetic resonance.

The duration and profile of the $B_1$ field bursts are carefully controlled. When a $B_1$ burst ends the logging tool antennae detect a signal, sometimes referred to as an echo, and generate an NMR signal indicative thereof. The time taken for the aforesaid signal to decay is referred to as the transverse relaxation time, denoted $T_2$.

$T_2$ is sometimes referred to as the "spin-spin" relaxation time. In practice in a logging tool a multi-stage burst is used because this tends to provide a series of readily detectable signal peaks (referred to as an "echo train") from which the $T_2$ amplitude may be calculated. In particular an initial RF emission that causes tilting of the spin axes of the protons by $\pi/2$ degrees is followed by a series of emissions that cause tilting by $\pi$ degrees. The decay following the latter is detectable and is measured by the logging tool in order to generate a series of signal amplitude peaks from which the value of $T_2$ can be derived.

The transverse relaxation time $T_2$ while typically of shorter duration than the longitudinal relaxation time $T_1$ also can be used to derive pore size information and information on pore fluid characteristics such as viscosity. The amplitude of the $T_1$ and $T_2$ relaxation time signals can be employed to derive a measure of the porosity of the formation.

The measurements taken using an NMR logging tool also can give rise to a coefficient of molecular diffusion (D) that in turn is useful in characterising the hydrocarbon-bearing fluids in the pores in the formation.

Use of an NMR logging tool therefore in theory can give rise to a three-dimensional dataset consisting of values related to $T_1$, $T_2$ and D. Such a dataset may be known as a three-dimensional kernel matrix where each entry corresponds to an NMR signal contribution from a unit of porosity for a specified ($T_1$, $T_2$, D) value tuple associated with a said entry. The signal contributions may be computed from fundamental equations that are well-known in the art.

The process of converting signal amplitude data generated in a logging tool into meaningful information that can be interpreted by a geoscientist or log analyst is sometimes referred to as "inversion". In many cases an aim of inversion is to uncover unknown physical properties from associated measurements. In the case of pulsed NMR interpretation, the goal of inversion is to find the fluid property distribution over the domain of ($T_1$, $T_2$, D) given the measured NMR log and knowing the underlying 3D kernel matrix.

Up to the present time it has not been possible to perform inversion on the full three-dimensional matrix in an acceptable timescale, that is a timescale that is regarded as desirable in downhole situations. Until now it has on the contrary been necessary to process 3D NMR signal contributions "offline", using inefficient non-linear optimisation techniques.

For reasons associated with the character of the fluids undergoing assessment it is however desirable to analyse NMR log data in real-time or near real-time (i.e. a relatively short time after the data have been generated).

Early in the development of pulsed NMR logging the computing power available either in on-board processing devices installed in the NMR logging tools, or in computers at surface locations and in communication with the logging tools, was not adequate to allow the inversion of large amounts of log data in real-time.

As a result geoscientists have historically confined themselves to inverting either the two-dimensional matrix constituted by the $T_1$ and $T_2$ data or the two-dimensional matrix constituted by the $T_2$ and D data, at least when wishing to process the data in real-time or near real-time.

More recently the ability of portable computers to resolve complex inversion problems has improved significantly. However real-time or near-real-time inversion of NMR measurements from three-dimensional kernel matrix has hitherto remained unattempted. Furthermore, characterization of inversion uncertainty due to the underdetermined nature of the NMR inversion problem has also remained unaddressed until now.

U.S. Pat. No. 5,517,115 to Prammer teaches an NMR data analysis technique in which a priori information about the likely nature of an NMR signal is modeled in advance of NMR logging activity. The modeled information is used in a constrained selection to approximate fluid properties from two-dimensional NMR log data.

Publication US 2013/0080058 discloses a method of processing log data obtained from three mutually orthogonal logging tool antennae but does not discuss the solution of NMR log inversion problems.

"A global inversion method for multi-dimensional NMR logging" [Sun et al, Journal of Magnetic Resonance 172 (2005) 152-160] describes an inversion technique for multi-dimensional NMR log information. This publication teaches the solving of a composite three-dimensional kernel that models the magnitude of NMR echoes detected by a logging tool.

U.S. Pat. No. 6,960,913 to Heaton contains a historical survey of single value decomposition (SVD) techniques for analysing NMR log data. The method claimed in U.S. Pat. No. 6,960,913 is stated to be independent of prior knowledge of fluid sample properties.

U.S. Pat. No. 6,937,014 to Sun et al discloses a method for obtaining a multi-dimensional proton density from a system of nuclear spins.

Other publications believed to be of background relevance to the field of the invention include U.S. Pat. Nos. 7,034,528, 7,388,374, 7,538,547, 7,565,833, 8,044,662, 8,633,691, 8,643,363 and 8,736,263 together with "A new inversion method for $(T_2, D)$ 2D NMR logging and fluid typing" [Tan et al, Computers and Geosciences 51 (2013) 366-380].

An aim of the invention is to solve or at least ameliorate one or more problems of prior art logging tools and associated methods of the kinds described herein.

BRIEF SUMMARY OF THE INVENTION

According to the invention in a first aspect there is provided a method of inverting three-dimensional fluid property distribution from NMR log data comprising the steps of:

a) causing an NMR logging tool to move along a borehole in a fluid-containing formation;

b) generating a static magnetic field and a sequence of magnetic pulses using the NMR logging tool such that the formation is subjected to static and pulsed magnetic energy emitted during movement of the NMR logging tool along the borehole;

c) detecting a plurality of NMR signals (y) resulting from interaction between the emitted magnetic energy and protons in the formation;

d) comparing the detected NMR signal values with a plurality of modeled signal values ($\hat{y}$) derived from precomputed values of NMR signal contributions, at points in the space spanned by $T_1$, and $T_2$, and diffusion values D;

e) identifying one or more said modeled signal values ($\hat{y}$) in respect of which an objective function involving a respective detected NMR signal value (y) and a said modeled signal value ($\hat{y}$) is optimised;

f) determining one or more optimal solution vectors φ corresponding to the optimized signal values ($\hat{y}$) at the aforesaid points in the space spanned by $T_1$, $T_2$ and D;

g) generating graphical, image log, tabular or digital information representative of the one or more properties of fluid in the formation; and h) displaying, printing, storing, transmitting or processing the graphical, image log, tabular or digital information.

The method of the invention may also include the further step of i) storing one or more of the detected NMR signal values.

The method of the invention through pre-computing of modeled signal values for the first time permits the rapid inversion of three-dimensional pulsed NMR signal contributions data (i.e. a 3D kernel matrix) of the kind explained herein. The method of the invention readily lends itself to linear programming techniques known in the art. The invention represents a significant step forward in the ability of geoscientists and log analysts to describe formation fluids based on NMR log data.

In a preferred embodiment of the invention the method includes the step j) of precomputing values of NMR signal contribution values at $(T_1, T_2, D)$ value tuples using the 3D kernel expression $$K_{[T_1, T_2, D]}(t) = K_{T_1}(t) K_{T_2}(t) K_D(t)$$

in which the value of each individual kernel of the kernel matrix at decay time t is given by $$K_{T_1}(t) = 1 - \exp\left(-\frac{WT_t}{T_1}\right)$$

$$K_{T_2}(t) = \exp\left(-\frac{t}{T_2}\right)$$

$$K_D(t) = \exp\left(-\frac{1}{12} \gamma^2 g^2 t_E^2 Dt\right)$$

wherein γ is a fundamental property of the protons in the fluid in the borehole; g is the gradient of the static magnetic field; $t_E$ is the inter-echo time as defined herein; and $WT_t$ is the wait time for magnetization before the particular decay associated with time tick t occurs.

By inter-echo time is meant the time between measurements of the decay curve. Typically the inter-echo time is the time between successive peaks in the decay curve.

Optionally the method of the invention includes the step k) of storing the precomputed NMR signal contribution values at $(T_1, T_2, D)$ value tuples as a three-dimensional matrix.

Further optionally the step e) of identifying one or more said modeled signal values ($\hat{y}$) in respect of which an objective function involving a respective detected NMR signal value (y) and a said modeled signal value ($\hat{y}$) is optimised includes evaluating the expression $o(y, \hat{y}) = \|y - \hat{y}\|_1$ wherein y is the NMR signal detected in step c); and $\hat{y}$ is the modeled counterpart signal derived from precomputed values of three dimensional NMR signal contribution values at $(T_1, T_2, D)$ value tuples in step d).

This aspect of the invention amounts to an optimisation step that readily lends itself to a linear programming approach therefore achieving global optimality in the solution and efficient runtimes contrarily to nonlinear optimization based approaches. The complexity of this optimization is a function of the problem size defined in terms of the size of the kernel matrix and the number of time stamps t. Whereas the number of time stamps is controlled by the application, the size of the precomputed kernel matrix may be pre-chosen. Kernel matrix size is typically determined by the desired resolution of the ($T_1$, $T_2$, D) domain. If such resolution prohibits fast optimization runtime, then effective data summary techniques on the kernel matrix values can be employed to circumvent the matrix size. This linear formulation permits the calculations forming part of the method of the invention to be completed in real-time or near-real-time. This is a particular advantage in the context of geological logging because it is usually strongly desirable to obtain log results as quickly as possible after log data are generated.

Using the said precomputed kernel matrix, the modeled NMR signal values may be obtained using an equation of the form:

$$\hat{y} = k \cdot \varphi$$

wherein k represents the kernel matrix of entries representing the signal contributions at pre-chosen ($T_1$, $T_2$, D) values and $\varphi$ represents a said vector of property values of the fluid/formation system at the pre-chosen ($T_1$, $T_2$, D) (step l) herein). Such an equation may be utilized to optimize any chosen objective function involving the measured NMR signal y and its modeled homologue $\hat{y}$.

The result of this optimization thus is an optimal solution vector $\varphi^*$. In a practical embodiment of the method of the invention plural instances of the solution vector $\varphi^*$ may be computed.

Conveniently the solution vector $\varphi$ optimizing the objective function o(y, $\hat{y}$) is constrained to take account of one or more physical requirements of the system under evaluation. Also conveniently the solution vector $\varphi$ optimizing the objective function o(y, $\hat{y}$) is further constrained to take account of a tendency of the solution vector to form a smooth surface when viewed in a three-dimensional space.

To this end the solution vector $\varphi$ is constrained according to:

$$\varphi_i \geq 0 \, \forall i$$

$$\Sigma_i \varphi_i \leq \varphi_{max}^\Sigma$$

$$|\Sigma_{\{i|i \text{ is even and } 1 \leq i \leq |\varphi^s|\}} \varphi_i^s - \Sigma_{\{i|i \text{ is odd and } 1 \leq i \leq |\varphi^s|\}} \varphi_i^s | \leq \tau \forall S$$

where s indexes any particular subset in the chosen partitioning of the solution vector's complete dimension set; $\varphi_{max}^\Sigma$ is the maximum total solution value and $\tau$ is a chosen smoothness factor.

Such constraints take account of physical truths of the system under evaluation, as set out in more detail below; and also take account of the tendency of fluid porosity values to form a smooth surface when viewed within a three-dimensional space as defined herein.

The method of the invention may include the further step of m) determining upper and lower bounds on any dimension or sum of dimensions of any optimal vector $\varphi^*$ residing in the set of optimal solutions for $\varphi$ optimizing the objective function o(y, $\hat{y}$). Thus the method of the invention includes defining an optimal solution space wherein each solution admits an optimal value for the chosen objective function and satisfies the constraints. Such upper and lower bounds amount to an interpretative benefit, and do not in themselves constrain the problem.

Furthermore the upper and lower bounds determined in step m) advantageously can be employed to characterize the uncertainty associated with any calculated optimal solution for $\varphi^*$ indicating a formation porosity distribution over the points $T_1$, $T_2$, D (step n) herein).

Additionally or alternatively the method may include the step of characterizing uncertainty of a calculated optimal vector $\varphi^*$ indicating a formation porosity distribution by seeking an optimal vector $\varphi^{**}$ the distance of which to $\varphi^*$ is maximal whereby to provide a measure of confidence in the respective optimal solutions $\varphi^*$ and $\varphi^{**}$.

Conveniently the method includes the steps p) of iteratively calculating a set of plural optimal solution vectors $\{\varphi^{*(n)}\}_n$ lying on the boundaries of the solution space and q) using the said set to provide one or more measures of confidence in any optimal solution.

Preferably $\varphi^{}$ is calculated (step r) herein) using the expression $$\varphi^{} = \underset{\varphi \in P}{\operatorname{argmax}} \|\varphi - \varphi^*\|_2^2$$

where P denotes the optimal solution space resulting from confining the solutions to the ones satisfying the constraints and admitting an optimal objective value.

Further preferably the method of the invention includes the step s) of calculating $\varphi^{*(n)}$ using the expression $$\varphi^{*(n)} = \underset{\varphi \in P}{\operatorname{argmax}} \left\| \varphi - \left( \underset{\substack{\Sigma_{i=1}^{n-1} \alpha_i = 1 \\ \alpha_i \geq 0}}{\operatorname{argmin}} \left\| \varphi - \sum_{i=1}^{n-1} \alpha_i \varphi^{*(i)} \right\|_1 \right) (\varphi^{*(i)} i = 1 \ldots n-1) \right\|_2^2$$

where P denotes the optimal solution space wherein any solution satisfies the domain constraints and admits an optimal objective value.

The method may also use the said optimal on-boundary solution set in a further step of fluid type identification and quantification with uncertainty analysis (step t) herein).

More specifically the step u) of defining the boundaries of the solution space containing the one or more optimal solutions may include iteratively determining at least one optimal vector $\varphi^{**}$ the distance of which from an optimal vector $\varphi^*$ is maximal, the method including iterating the determination of optimal vectors $\{\varphi^{*(n)}\}_n$ such that the span of their convex hull is maximized in each iteration, continuing the iterative process until the increase in new gained span of the convex hull of the generated optimal solution set $\{\varphi^{*(n)}\}_n$ becomes less than a respective predetermined amount; labeling each optimal solution in the generated solution set (i.e. defining the boundaries to the solution space) according to the fluid types present therein; and calculating the volume of each of the one or more fluid types in each of the enumerated optimal solutions (i.e. defining the convex hull of the solution space). Thus the method of the invention involves classifying fluids and quantifying their volumes using the solutions lying on the boundaries of the optimal solution space. This, in turn, allows for fluid classification and volume quantification under uncertainty of the inversion. This is somewhat in contrast to prior art algorithmic fluid typing and quantifying techniques based on deterministic inversion methods (i.e. producing a single solution and not accounting for uncertainty of the inversion).

Alternatively the step of defining the boundaries of the solution space containing the one or more optimal solutions may include (step v) herein) selecting, based on prior domain knowledge, one or more extreme solutions guaranteed to lie outside the solution space; projecting the extreme solutions onto the solution space in order to define the boundaries of the space; labeling each optimal solution in the generated solution set defining the set of all boundaries to the solution space according to fluid types present therein; and calculating the volume of each of the one or more fluid types in each enumerated optimal solution in the optimal solution set $\{\varphi^{*(n)}\}_n$ collectively defining the boundaries of the solution space.

Furthermore, quantification of the fluid volumes for each of the optimal solutions in the enumerated optimal solution set defining the boundaries of the solution space leads to a probabilistic characterization of the volume of any identified fluid type via analyzing the point set distribution over the solution space defined by the enumerated solution set defining its convex hull.

Conveniently the method of the invention includes the step w) of using the identified and volume-quantified optimal on-boundary solutions to characterize the volumetric distribution of each identified fluid.

The invention is also considered to reside in apparatus for performing a method as aforesaid. Thus in a further aspect of the invention there is provided apparatus for inverting 3-dimensional fluid property distribution from NMR log data comprising:

a) an NMR logging tool that is capable of moving along a borehole in a fluid-containing formation, the NMR logging tool including one or more generators of a static magnetic field that are emissive into the formation; one or more generators of a sequence of magnetic pulses that are emissive into the formation; and one or more antennae that detect NMR signals resulting from interaction between the emitted magnetic energy and protons in the formation and generate NMR signals therefrom; and b) one or more programmable devices that is programmed to:

c) compare the detected NMR signal values with a plurality of modeled signal values ($\hat{y}$) derived from precomputed values of NMR signal contributions at points in the space spanned by $T_1$, $T_2$, and D;

d) identify one or more said modeled signal values ($\hat{y}$) in respect of which a an objective function involving a respective detected NMR signal value (y) and a said modeled signal value ($\hat{y}$) is optimised;

e) determine one or more optimal solution vectors $\varphi$ corresponding to the optimized signal values ($\hat{y}$) at the aforesaid points in the space spanned by $T_1$, $T_2$ and D space;

f) generate graphical, tabular or digital information representative of the one or more properties of fluid in the formation; and g) display, print, store, transmit or process the graphical, tabular or digital information.

Further features of the apparatus of the invention are analogous to the aspects of the method of the invention as set out herein.

For the avoidance of doubt, the programmable device forming part of the apparatus of the invention may be integral with the remainder of the apparatus; or may lie remote therefrom but nonetheless able to process signal data generated by the NMR logging tool. The programmable device may be connected to the remainder of the apparatus e.g. by way of a cable that transmits signals as described herein to the programmable device. Alternatively the programmable device may receive the signals through use of any of a range of wireless communication methods as will be known to the person of skill in the art.

The method and apparatus of the invention beneficially provide an effective means of inverting three-dimensional NMR signal contributions data in a timescale that is acceptable in downhole logging applications, and without requiring excessive (costly) computing resources.

The method and apparatus of the invention are applicable in a wide variety of NMR logging situations, including but not limited to those summarised herein.

BRIEF DESCRIPTION OF THE DRAWINGS

There now follows a description of preferred embodiments of the invention, by way of non-limiting example, with reference being made to the accompanying drawings in which.

DETAILED DESCRIPTION OF THE INVENTION

Figure 1:
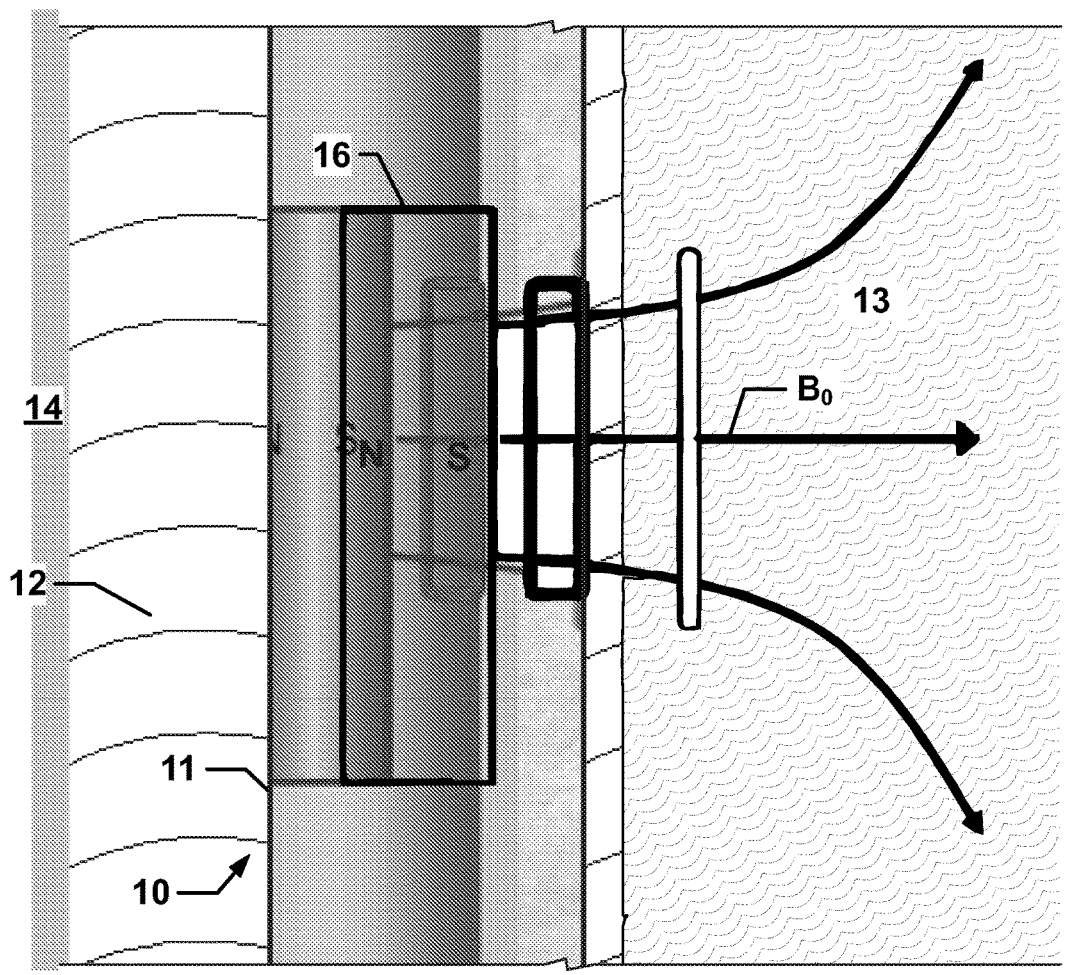
FIG. 1 is a schematic, simplified view showing operation of one form of NMR logging tool.

Referring to the drawings FIG. 1 shows in a simplified form the nature and operation of one type of NMR logging tool 10.

Logging tool 10 as illustrated includes an elongate cylindrical body 11 that is inserted into, and may move along, a borehole 12 formed in a formation 13 it is required to assess e.g. from the standpoint of its ability to yield useful hydrocarbons.

As is typically the case formation 13 is porous. A hydrocarbon-bearing fluid, or more typically a mixture of fluids, is distributed in the pores. Among other characteristics of the formation fluid it is desired to assess its hydrogen (proton) content and its viscosity. These parameters are important when making an assessment of the make-up of the formation fluid, and in particular whether it includes useable oil or gas.

It is also desired to assess the porosity of the formation 13 itself. One reason for this is that porosity data can indicate whether the extraction of formation fluid(s) is likely to be straightforward or problematic. A formation porosity value also can be used to provide a volumetric estimate of formation fluid(s). Such estimating may include partitioning of different fluids into respective volumes.

An NMR logging tool is able to assist in all such assessments as aforesaid.

Figure 2:
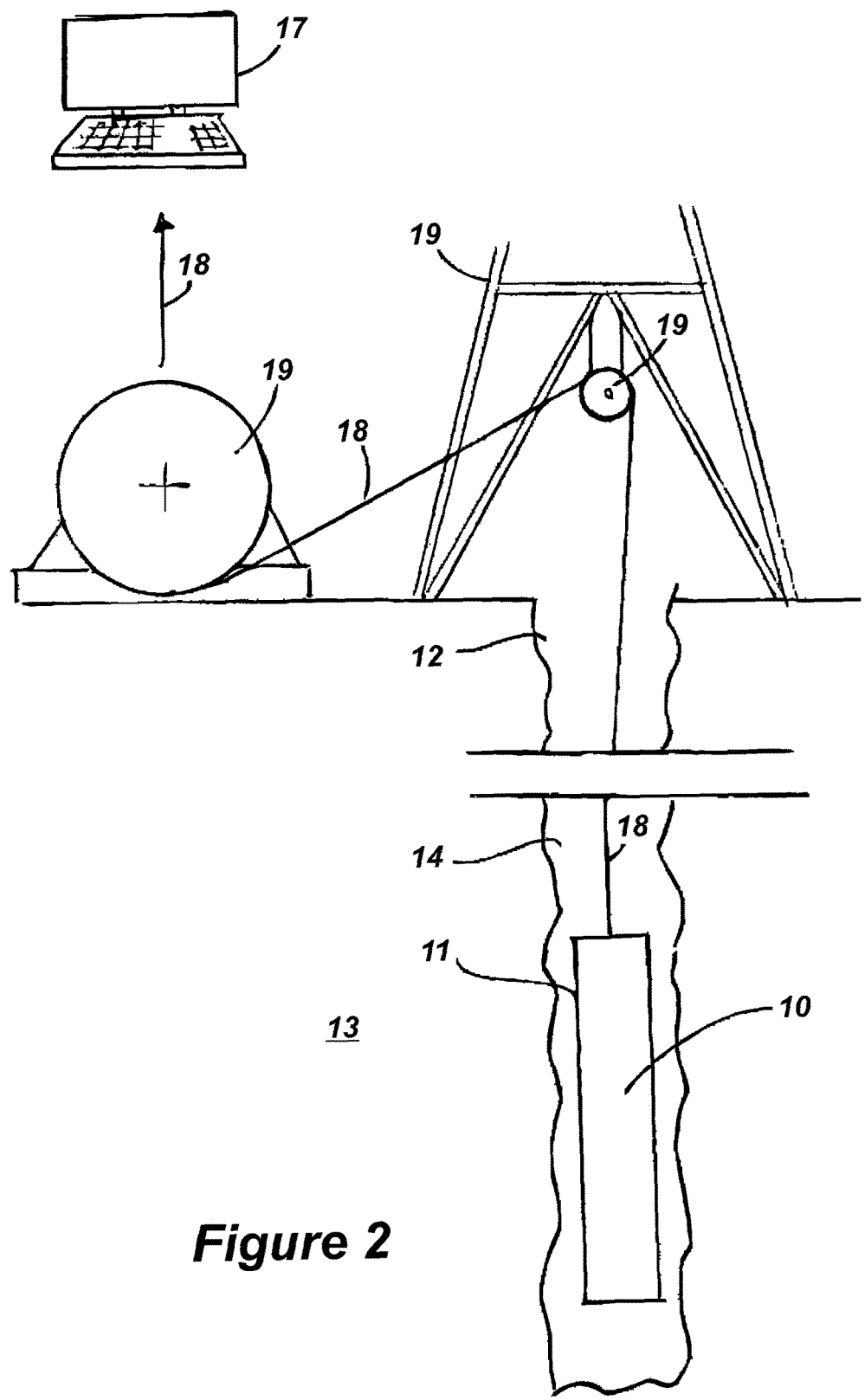
FIG. 2 shows in outline form further apparatus forming part of the invention.
Figure 3:
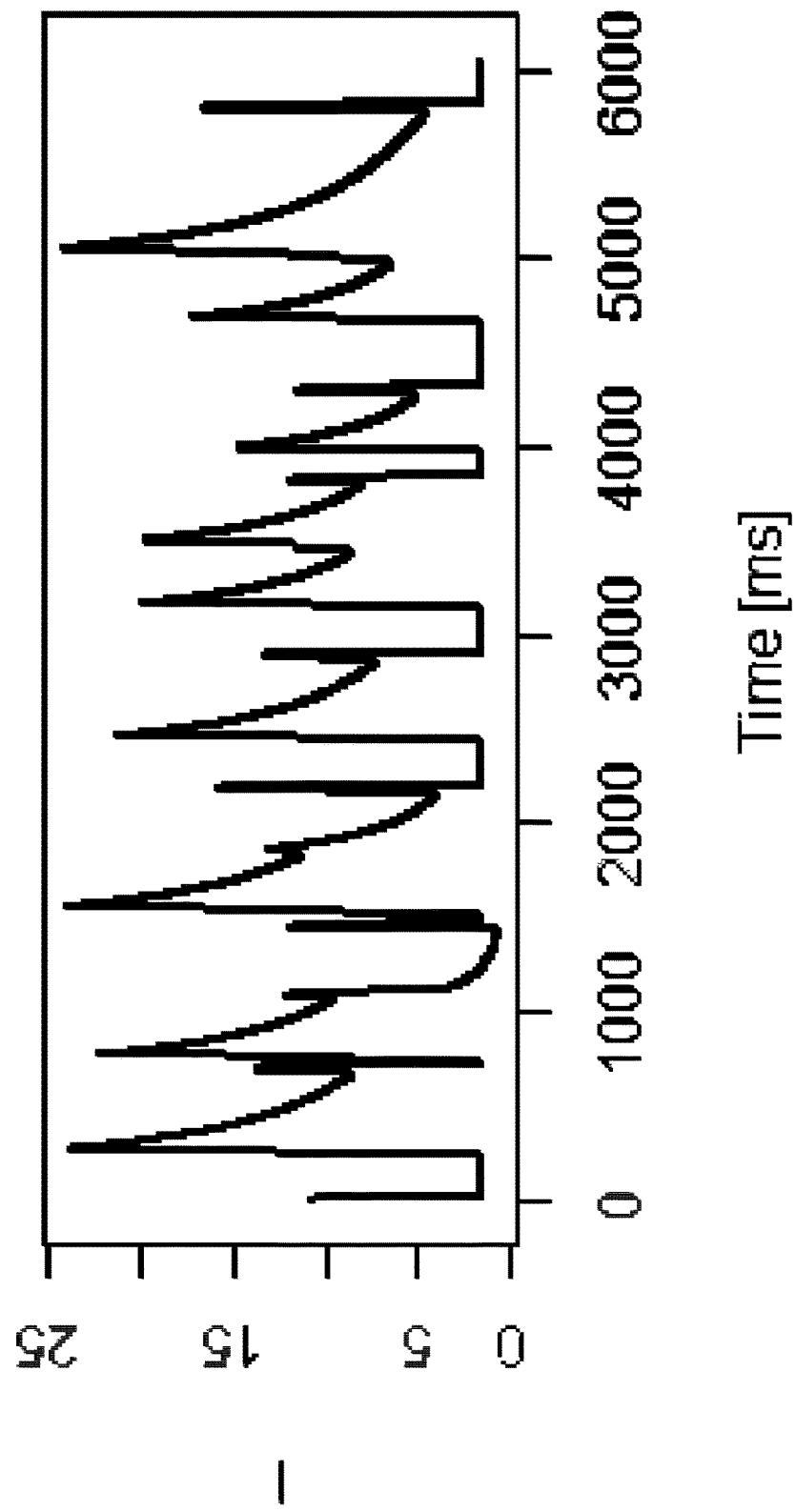
FIG. 3 is an exemplary plot of the output of a typical NMR logging tool such as that shown in FIG. 1.
Figure 4:
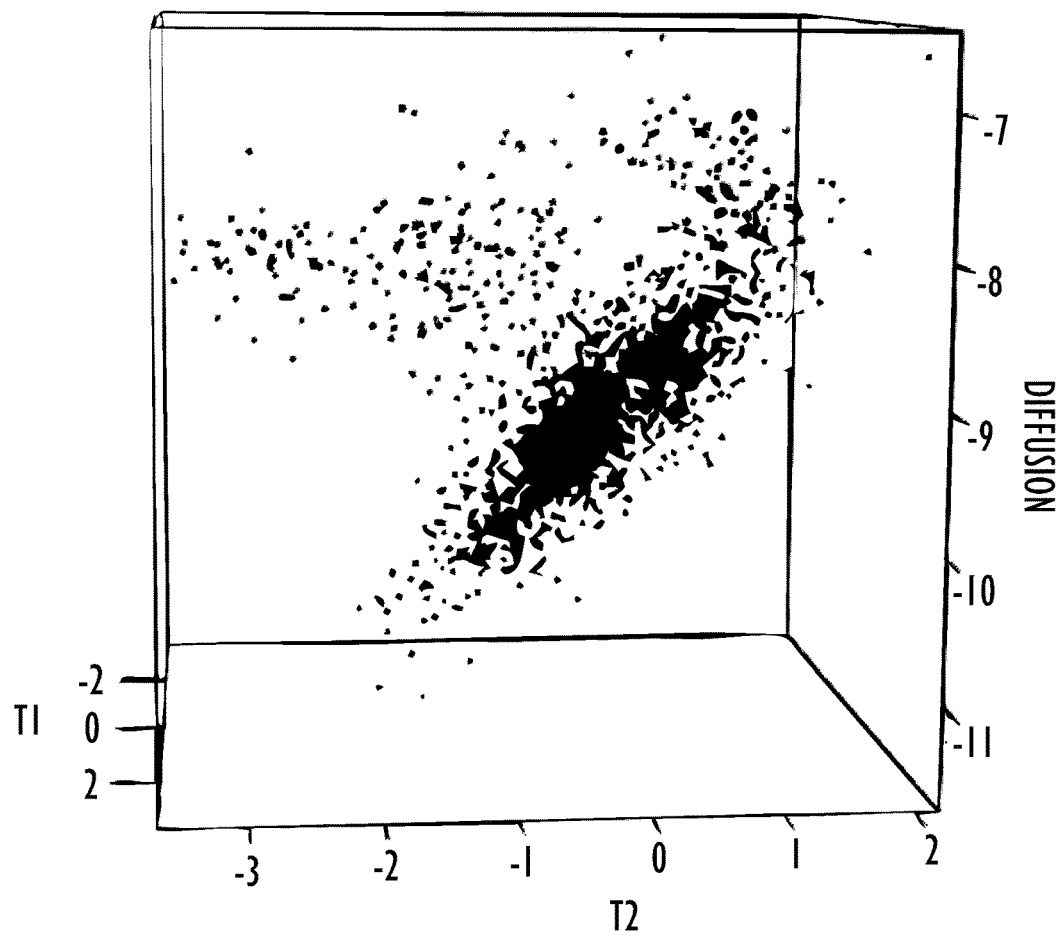
FIG. 4 is a representation of a three-dimensional fluid property distribution over $T_1$, $T_2$ and D that interprets the output plot of FIG. 3.
Figure 5:
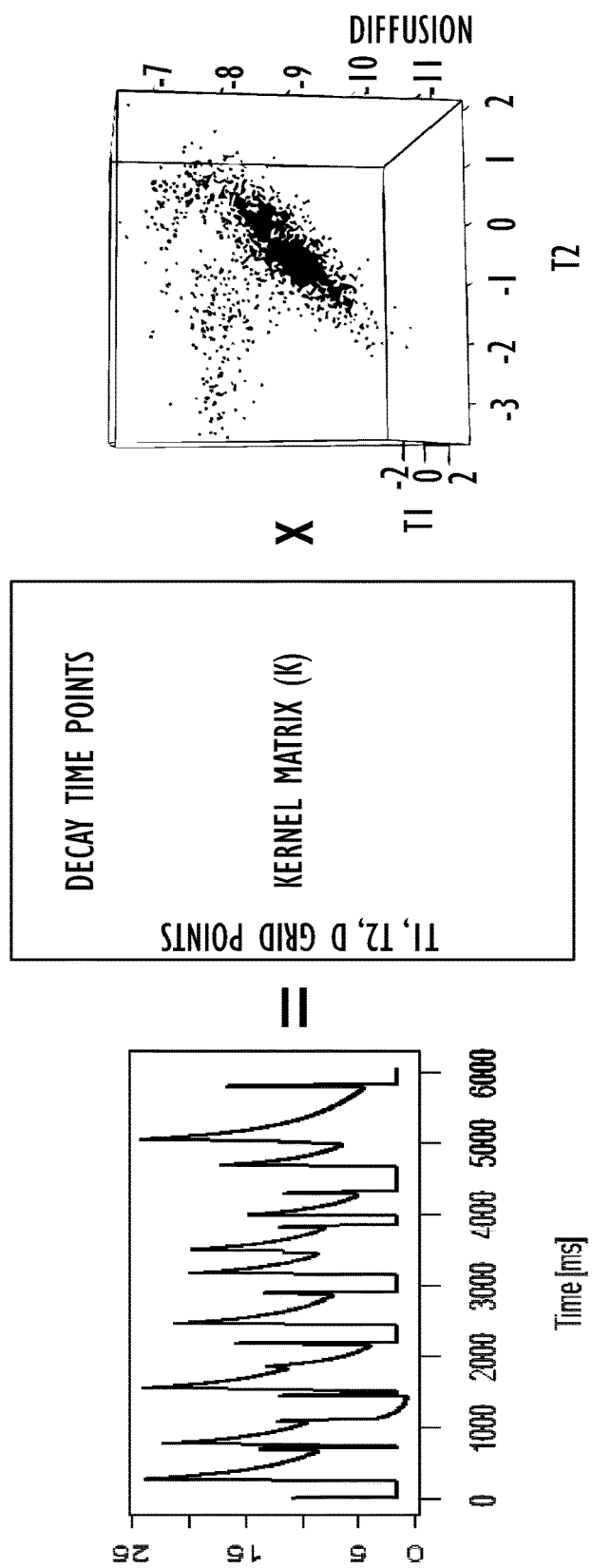
FIG. 5 illustrates in graphical form an expression that makes up the output plot of FIG. 3 and that illustrates the fundamental equation relating the NMR measurements and the associated fluid properties to be inverted.

As best illustrated schematically in FIG. 2 the NMR logging tool 10 is operatively connected, or at least is connectable, to communicate with a programmable device that in the embodiment shown takes the form of a personal computer 17 (although other forms of programmable device are possible within the scope of the invention). FIG. 2 shows the logging tool 10 connected to the computer by wireline 18 that is paid out into the borehole 12 by way of per se known paying out and rewinding equipment 19.

As is known to the person of skill in the art numerous variations on the simple logging tool connection arrangement are possible. FIG. 2 represents one exemplary and non-limiting way in which the logging tool 10 may communicate with a programmable device located at a surface location.

It is not however essential that wireline is the chosen method of connection; or that the programmable device is located externally of the borehole 12 as shown. On the contrary it is possible for instance for the programmable device to be located partly or entirely in a downhole location, for example forming part of a logging or drill string. All such variants are within the scope of the invention. The programmable device does not have to be in the personal computer configuration shown. Moreover various wireless communication methods are possible for causing communication between the logging tool 10 and a remotely located programmable device 17 when it is not possible or desired to use wireline or a similar connecting cable.

FIGS. 1 to 5 show a so-called pulsed NMR logging tool 10. The principles of the invention as broadly stated herein are applicable to NMR logging tools other than of the pulsed type, although the techniques of the invention have been developed specifically with pulsed NMR logging tool characteristics in mind.

The borehole 12 is shown in FIG. 1 as a straight, parallel-sided, vertically extending bore. This however represents a highly idealized situation for illustration purposes. In practice the borehole 12 may not be vertical (and indeed may extend e.g. inclinedly or horizontally); it is unlikely to be completely straight; and so-called "squeezing" of the borehole walls or other forms of collapse may lead it not to be parallel-sided as illustrated. In consequence the rugose borehole shown in FIG. 2 may therefore be a more realistic representation. The invention is applicable in respect of all boreholes in which an NMR logging tool is useable, including non-idealized boreholes such as those described above or shown in FIG. 2.

The borehole 12 in the example shown is filled with borehole fluid 14 which may be a drilling mud, a chemical introduced into the borehole in order to achieve certain effects as will be known to the person of skill in the art, water, brine, oil, tar, one or more gases or (very commonly) mixtures and/or solutions of two or more of the aforesaid components.

In use of the NMR logging tool 10 the cylindrical body 11 is conveyed inside the borehole e.g. supported on wireline or on drill pipe to a chosen location that can be identified by any of a range of techniques known to a logging tool operator.

As explained hereinabove, the NMR logging tool 10 includes one or more magnets 16 the purpose of which is to emit a static magnetic field $B_0$ into the formation 13 as illustrated in FIG. 1. This magnetic field on emission aligns (polarizes) protons in the formation fluid from a random (resting) state to the direction of the imposed $B_0$ magnetic field.

It takes a certain time for the protons to become aligned in this way following the application of the static magnetic field. This time is the longitudinal relaxation time $T_1$ described above.

Following alignment the protons precess towards the un-polarized, random state in accordance with the known operational principles of NMR devices.

Precession of the protons gives rise to a detectable, decaying magnetic field. One or more antennae in the logging tool 10 detect the decaying magnetic field, which is related to the $T_1$ time by a known expression. The antennae, which are omitted from the drawings for ease of study, generate signals (voltages) indicative of the detected magnetic field values.

The logging tool 10 as explained also generates short bursts of RF energy that give rise to an oscillating magnetic field $B_1$, tilting the aligned protons as previously explained and causing them to precess in phase to one another.

The duration and profile of the $B_1$ field burst are carefully controlled, again as described above. A typical burst from one known NMR logging tool has a peak power in the tens of kW and an amplitude in excess of 1000 volts. Other burst parameters are possible depending on the design of the logging tool 10, and its programming. Typically a series of bursts is used to give rise to an echo train.

When each pulse of the $B_1$ burst ends the logging tool antennae detect a signal (echo), and generate NMR signals (voltages) indicative thereof. The $T_2$ relaxation time explained above can be derived from such signals, which usually are great in number.

Following the generation of signals in the aforesaid manner the logging tool is moved to a fresh location in the borehole and the aforesaid steps repeated. Usually the logging tool is initially deployed to a maximal depth in the borehole and gradually withdrawn towards the surface, collecting and/or transmitting data each time it halts by way of the aforesaid sequence of steps or variants thereof.

As noted the signals generated by the antennae can be modeled using a three-dimensional NMR signal contribution dataset (kernel matrix). Hitherto it has not been possible to invert the fluid property distribution given the three-dimensional data matrix and the measured NMR logs (signals) while simultaneously taking account of all three dimensions of the 3-tuple ($T_1$, $T_2$, D) without any a priori assumptions and/or in an acceptable timescale to provide real-time or near real-time logging.

Processing of the signals generated by the NMR logging tool is carried out by the programmable device 17 in accordance with the method steps set out below.

The fundamental equation relating the desired fluid properties (i.e., $T_1$, $T_2$, and D) to the measured NMR signal at any particular time tick is characterized via a linear map. In particular, the value of the NMR signal at any given time tick is modeled as the inner product of the kernel vector (linearly indexed kernel matrix) at the underlying time tick and the fluid property vector.

For a fixed time tick t, the kernel vector, denoted $k_t = (k_{t,i})_i$, may be precomputed from a known physical model. Each dimension i in the kernel vector is completely determined by a particular choice for the 3-tuple ($T_1$, $T_2$, D). More generally, given a sufficiently fine discretization of the 3D box (i.e., orthogonally delimited space) occupied by ($T_1$, $T_2$, D) then each dimension i serves as a linearized index for a particular 3D grid cell and $k_{t,i}$ is directly computable from the value tuple ($T_1$, $T_2$, D) at the grid cell indexed by i and for time tick t. Formally, if $\hat{y}_t$ stands for the modeled observation at time tick t and $\varphi$ for the fluid property vector then, $$\hat{y}_t = k_t \cdot \varphi = \Sigma_i k_{t,i} \varphi_i$$

Optimization Objective

Let $y_t$ denote the tool-measured signal value at time tick t. As $\hat{y}_t$ should, in theory, "mimic" $y_t$ for all time ticks, we presume some objectively defined similarity (distance) function between the observed and modeled signals i.e., $o(y, \hat{y})$ where $y=(y_t)_t$ and $\hat{y}=(\hat{y}_t)_t$ Hence, the method of the invention seeks $\hat{y}$ that minimizes $o(y, \hat{y})$ and therefore inferring the property vector $\varphi$ is amenable to an optimization problem.

Although the method of the invention is not bound to any particular choice of $o(\cdot)$, a preferred embodiment chooses $o(y, \hat{y})=\|y-\hat{y}\|_1$ i.e., the similarity between any two signals is assessed in terms of the first norm of their difference.

Optimization Constraints

The solution vector $\varphi$ must satisfy some a priori domain constraints. Since, for all indices i, $\varphi_i$ represents a porosity value, we have $\varphi_i \geq 0 \;\forall\; i$. Furthermore, the sum of all porosities cannot exceed 100% by definition, i.e. $\Sigma_i\; \varphi_i \leq 100$. More generally, we denote the maximum total porosity value with $\varphi_{max}^\Sigma$.

In addition to the physical constraints above, experience suggests that fluid porosity values form a smooth surface when viewed within the 3D box over all values for $(T_1, T_2, D)$. Smoothness constraints should therefore help refine further the set of all allowed solutions.

Consider a 3D-equivalent representation of $\varphi$, i.e. $\varphi=(\varphi_{i,j,k})_{i,j,k}$. The first order-smoothness constraint may be defined as $$\left| \frac{\varphi_{i,j,k} - \varphi_{i',j',k'}}{(T_{1_i} - T_{1_{i'}})(T_{2_j} - T_{2_{j'}})(D_k - D_{k'})} \right| \leq \delta$$

for any two neighboring grid cells of indices (i, j, k) and (i', j', k') in the 3D grid space i.e., $\|(i, j, k)-(i', j', k')\|_\infty=1$ and where $\delta$ is a threshold defining the smoothness factor. The first-order smoothness constraint is defined by analogy to first-order function smoothness using the finite-difference instead of the exact derivative. A similar construction can be done for the second-order smoothness constraint to get $$\left| \frac{\frac{\varphi_{i,j,k} - \varphi_{i',j',k'}}{(T_{1_i} - T_{1_{i'}})(T_{2_j} - T_{2_{j'}})(D_k - D_{k'})} - \frac{\varphi_{i',j',k'} - \varphi_{i'',j'',k''}}{(T_{1_i} - T_{1_{i'}})(T_{2_j} - T_{2_{j'}})(D_k - D_{k'})}}{(T_{1_i} - T_{1_{i''}})(T_{2_j} - T_{2_{j''}})(D_k - D_{k''})} \right| \leq \delta$$

where $\|(i, j, k)-(i', j', k')\|_\infty=1$, $\|(i', j', k')-(i'', j'', k'')\|_\infty=1$ and $\|(i, j, k)-(i'', j'', k'')\|_\infty=2$. This construction may be recursively repeated for any desired maximum smoothness order.

As the complexity of the number of smoothness constraints can become prohibitively large even for a small maximum smoothness order, the method of the invention includes an alternate approximation scheme in a preferred embodiment.

Consider again the vectorized representation of $\varphi$ i.e., $\varphi=(\varphi_i)_i$ and choose an m-partitioning of the $\varphi$ vector's indices denoted $\{\varphi^1, \varphi^2, \ldots, \varphi^m\}$ and where the subsets in the partitioning are contiguous collections of indices possibly overlapping. Then for any partition subset $\varphi^s$, it is possible to impose the following constraint to implicitly control the smoothness of any solution. Precisely, it can be expected that the sum of all porosities over all odd indices in any partition subset is approximately equal to the sum over the even indices of the same partition subset. Formally, $\forall s, |\Sigma_{\{i|i \text{ is even and } 1\leq i\leq|\varphi^s|\}}\varphi_i^s - \Sigma_{\{i|i \text{ is odd and } 1\leq i\leq|\varphi^s|\}}\varphi_i^s| \leq \tau$ where $\tau$ is some chosen smoothness factor.

Optimization Problem

Succinctly, computing an optimal $\varphi$ may be reduced to computing the following optimization problem, $$\varphi^* = \underset{\varphi}{\operatorname{argmin}} \|y - \hat{y}\|_1$$

$$\text{subject to} \begin{cases} \hat{y}_t = \sum_i k_{t,i}\varphi_i \\ \varphi_i \geq 0 \;\forall\; i \\ \sum_i \varphi_i \leq \varphi_{max}^\Sigma \\ \left| \sum_{\{i|i \text{ is even and } 1\leq i\leq|\varphi^s|\}} \varphi_i^s - \sum_{\{i|i \text{ is odd and } 1\leq i\leq|\varphi^s|\}} \varphi_i^s \right| \leq \tau \;\forall\; s \end{cases}$$

The above constrained optimization problem can be cast almost immediately to a linear programming (LP) problem and thus any of the known LP solvers can be used to solve it.

Optimal Solution Space Characterization and Uncertainty Analysis

Let $o^* = \|y-\hat{y}\|_1 = \|y-\Sigma_i k_{t,i}\varphi_i^*\|_1$ be the optimal objective value. Then, the space of all optimal solutions (i.e., admitting $o^*$ as their objective value) is the polytope P satisfying, $$P = \left\{ \varphi^* \;\middle|\; \begin{array}{c} o^* = \|y - \Sigma_i k_{t,i}\varphi_i^*\|_1, \\ \varphi_i^* \geq 0 \;\forall\; i, \\ \Sigma_i \varphi_i^* \leq \varphi_{max}^\Sigma, \\ |\Sigma_{\{i|i \text{ is even and } 1\leq i\leq|\varphi^{*,s}|\}}\varphi_i^{*,s} - \Sigma_{\{i|i \text{ is odd and } 1\leq i\leq|\varphi^{*,s}|\}}\varphi_i^{*,s}| \leq \tau \;\forall\; s \end{array} \right\}$$

Fix a cell of linear index i. Then any optimal $\varphi_i^*$ admits lower and upper bounds, respectively, $l_i$ and $u_i$. Such bounds may be computed by solving the following two optimization problems.

$$l_i = \min_{\varphi^* \in P} \varphi_i^* \text{ and } u_i = \max_{\varphi^* \in P} \varphi_i^*$$

The bounds $l_i$ and $u_i$ may be used as a direct characterization of the uncertainty on the porosity value at of any cell of chosen index i. More generally, given any desired region of interest defined via a collection C of cell indices, the uncertainty in the total porosity over C may be similarly characterized via the following bounds, $$(l_c, u_c) = \left( \min_{\varphi^* \in P} \sum_{i \in C} \varphi_i^*, \max_{\varphi^* \in P} \sum_{i \in C} \varphi_i^* \right)$$

One additional characterization of uncertainty with respect to any chosen optimal solution $\varphi^*$ may be done by seeking an optimal solution $\varphi^{**}$ admitting maximum distance to $\varphi^*$. If the distance measure is taken to be the square of the second norm of the difference then computing $\varphi^{}$ reduces to, $$\varphi^{} = \underset{\varphi \in P}{\operatorname{argmax}} \|\varphi - \varphi^*\|_2^2$$

The maximized discrepancy between the two optimal solutions φ* and φ** provides a type of confidence measure in choosing either of such two optimal solutions. More generally, computing a set of iteratively generated new optimal solution instances i.e. $\{\varphi^{*(n)}\}_n$ may be performed according to the next section and the entire set can be collectively used to provide a confidence measure around any particularly chosen optimal solution.

Fluid Typing with Uncertainty Analysis

The previous section showed that any optimal solution (porosity vector) lives in a bounded polytope P of dimension on the order of the number of grid cells. Furthermore, given any prefixed grid region of interest, minimum and maximum total porosity volumes may be computed considering all solutions residing in P by solving the associated optimization problems. A potential difficulty is that whereas it is possible to compute volumes and volume bounds over any chosen regions, such regions may be completely arbitrary and cannot be directly mapped to a fluid label. A systematic scheme for fluid labeling that can be coupled with this framework is therefore required.

The method of the invention therefore additionally includes enumeration of a sufficient number of solutions lying on the boundary of the solution space P (vertices). The enumerated solutions would provide a sufficiently accurate approximation to the convex hull of P computable within a given time budget. Two possible schemes for the approximate vertex enumeration problem are:

i. Generalizing the maximum distance principle outlined in the previous section to iteratively generate vertices so that the span of the approximating convex hull at each iteration is maximally increased (greedy strategy), with the process terminating when either any additional gained space span becomes negligible or when a time budget is exhausted. Computing the $n^{th}$ instance of the optimal solution according the aforesaid principle amounts to solving the following optimization problem:

$$\varphi^{*(n)} = \underset{\varphi \in P}{\mathrm{argmax}} \left\| \varphi - \left( \underset{\substack{\Sigma_{i=1}^{n-1} \alpha_i = 1 \\ \alpha_i \geq 0}}{\mathrm{argmin}} \left\| \varphi - \sum_{i=1}^{n-1} \alpha_i \varphi^{*(i)} \right\|_1 \right) (\varphi^{*(i)})_{i=1 \ldots n-1} \right\|_2^2$$

Formally stated, the iterative process of computing $\varphi^{*(n)}$ continues until at some iteration n and for some sufficiently small threshold ε, the maximized minimum distance to the current convex hull from any optimal solution satisfies, $$\underset{\varphi \in P}{\max} \left\| \varphi - \left( \underset{\substack{\Sigma_{i=1}^{n-1} \alpha_i = 1 \\ \alpha_i \geq 0}}{\mathrm{argmin}} \left\| \varphi - \sum_{i=1}^{n-1} \alpha_i \varphi^{*(i)} \right\|_1 \right) (\varphi^{*(i)})_{i=1 \ldots n-1} \right\|_2^2 \leq \varepsilon$$

ii. Using prior domain knowledge to pick trivial extreme solutions (guaranteed to lie outside of any solution space boundaries) and then projecting the said solutions onto P to represent the set of approximating vertices which are evidently made to satisfy all of the constraints in P. The convex hull of the projected vertices is then used to define the approximating solution space which becomes a sufficient surrogate for the entire collective set of constraints (defining the optimal solution space) previously incorporated. The runtime of this method is well-controlled in advance since the number of initial extreme solutions can be pre-chosen.

The method then proceeds by labeling each solution in the enumerated vertex set. This method is not bound to any particular fluid labeling scheme given an input solution. Rather, the method of the invention presumes a readily existing fluid labeling method and exploits it to label the computed vertex set. Any such labeling method does not have to produce "crisp" (i.e., deterministic) target fluid labels. Rather the labeling can be probabilistic. Therefore, assuming the vertex solutions are adequately labeled (possibly probabilistically), the total volume for each fluid type in each of the vertex solutions is calculated. Next, the vertex set can be interpreted in terms of the computed fluid volumes and therefore from the standpoint of the answer product, the result is a vertex set defining a bounded polytope in 3D space (since three fluid types i.e., gas, water, and oil, are expected). If the vertices in the vertex set are computed probabilistically then any point in the bounded 3D polytope admits a weight value; otherwise all points have a uniform weight distribution. The final answer product can be visualized as a bounded 3D polytope with a heatmap in its inside illustrating the probability of any optimal solution. In addition to this visual answer product, queries can be performed to give answers to questions of the following forms:

What is the complete volume range of a specified fluid type?

What is the confidence range of a specified fluid type based on a specified confidence level?

What is the probabilistic range distribution of a specified fluid type?

What is the likelihood that we have a specified minimum volume of a specified fluid type?

The programmable device in a preferred embodiment of the apparatus of the invention includes programming aimed at carrying out the foregoing method steps.

Preferences and options for a given aspect, feature or parameter of the invention should, unless the context indicates otherwise, be regarded as having been disclosed in combination with any and all preferences and options for all other aspects, features and parameters of the invention.

The listing or discussion of an apparently prior-published document in this specification should not necessarily be taken as an acknowledgement that the document is part of the state of the art or is common general knowledge.

The invention claimed is:

1. A method of evaluating for fluid in a fluid-containing formation intersected by a borehole, the method comprising the steps of:

logging the borehole in the fluid-containing formation by operating a Nuclear Magnetic Resonance (NMR) logging tool along the borehole in the fluid-containing formation, the logging comprising:

generating a static magnetic field and a sequence of magnetic pulses using the NMR logging tool such that the fluid-containing formation is subjected to static and pulsed magnetic energy emitted during movement of the NMR logging tool along the borehole; and detecting, using the NMR logging tool, an NMR signal (y) of NMR log data resulting from interaction between the emitted magnetic energy and protons in the fluid-containing formation; and imaging the NMR log data of the fluid-containing formation with one or more programmable devices by inverting a three-dimensional fluid property distribution of fluid in the fluid-containing formation from the NMR log data, the imaging comprising:

comparing, using one or more programmable devices, the detected NMR signal (y) with a plurality of modeled signals (ŷ) derived from precomputed values of NMR signal contributions at points in a solution space spanned by longitudinal relaxation time $T_1$, transverse relaxation time $T_2$, and coefficient of molecular diffusion D;

identifying, using the one or more programmable devices, one or more said modeled signals (ŷ) in respect of which an objective function o(y, ŷ) involving a respective detected NMR signal (y) and said modeled signal (ŷ) is optimized;

determining, using the one or more programmable devices, one or more optimal solution vectors φ corresponding to the one or more optimized signals (ŷ) at the aforesaid points in the solution space spanned by $T_1$, $T_2$ and D; and generating, using the one or more programmable devices from the determination, image information representative of one or more properties of the fluid in the fluid-containing formation; and assessing the fluid in the formation from the image information by defining boundaries of the solution space containing the one or more optimal solution vectors φ, and using said bounded solution space in a further step of fluid type identification and volume quantification with uncertainty analysis.

2. The method according to claim 1, comprising the further step of storing one or more values of the detected NMR signal.

3. The method according to claim 1, further comprising the step of precomputing values of NMR signal contribution values at ($T_1$, $T_2$, D) value tuples using the three-dimensional kernel expression $$K_{[T_1,T_2,D]}(t)=K_{T_1}(t)K_{T_2}(t)K_D(t)$$

in which the value of each individual kernel for computing the kernel matrix at decay time t is given by $$K_{T_1}(t) = 1 - \exp\left(-\frac{WT_t}{T_1}\right)$$

$$K_{T_2}(t) = \exp\left(-\frac{t}{T_2}\right)$$

$$K_D(t) = \exp\left(-\frac{1}{12}\gamma^2 g^2 t_E^2 Dt\right)$$

wherein γ is a fundamental property of the protons in the fluid in the borehole; g is the gradient of the static magnetic field; $t_E$ is the inter-echo time as defined herein; and $WT_t$ is the wait time for magnetization before the particular decay associated with time tick t occurs.

4. The method according to claim 1, further comprising the step of storing the precomputed NMR signal contribution values at ($T_1$, $T_2$, D) value tuples as a three-dimensional matrix.

5. The method according to claim 1, wherein the step of identifying one or more said modeled signal values (ŷ) in respect of which the objective function o(y, ŷ) involving the respective detected NMR signal (y) and said modeled signal (ŷ) is optimised comprises evaluating the objective function o(y, ŷ)=∥y−ŷ∥₁; wherein y is the NMR signal detected; and wherein ŷ is the modeled counterpart signal derived from precomputed values of three dimensional NMR signal contribution values at ($T_1$, $T_2$, D), value tuples.

6. The method according to claim 1, further comprising the step of using the precomputed NMR signal contribution values at the ($T_1$, $T_2$, D) value tuples to obtain modeled NMR signal values using an equation of the form:

$$\hat{y}=k\cdot\varphi$$

wherein k represents a kernel matrix of entries representing the signal contributions at pre-chosen ($T_1$, $T_2$, D) value tuples; and wherein φ represents said property vector of the fluid/formation system.

7. The method according to claim 1, wherein the solution vector optimizing the objective function o(y, ŷ) is constrained to take account of one or more physical constraints of the system under evaluation.

8. The method according to claim 1, wherein the solution vector optimizing the objective function o(y, ŷ) is constrained to take account of a tendency of the solution vector to form a smooth surface when viewed in a three-dimensional space.

9. The method according to claim 1, wherein the solution vector φ optimizing the objective function o(y, ŷ) is constrained according to:

$$\varphi_i \geq 0 \forall i$$

$$\Sigma_i \varphi_i \leq \varphi_{max}^\Sigma$$

$$|\Sigma_{\{i|i \text{ is even and } 1\leq i\leq|\varphi^s|\}}\varphi_i^s - \Sigma_{\{i|i \text{ is odd and } 1\leq i\leq|\varphi^s|\}}\varphi_i^s| \leq \tau \forall S,$$

where s indexes any particular subset in the chosen partitioning of the solution vector's complete dimension set; $\varphi_{max}^\Sigma$ is the maximum total solution value and τ is a chosen smoothness factor.

10. The method according to claim 1, further comprising the further step of determining upper and lower bounds on any dimension or sum of dimensions of the vector φ residing in the set of optimal solutions for φ optimizing the objective function o(y, ŷ).

11. The method according to claim 1, further comprising the further step of determining upper and lower bounds on any dimension or sum of dimensions of any optimal solution for φ optimizing the objective function o(y, ŷ) and using the determined upper and lower bounds to characterize the uncertainty in the calculated optimal solution for φ indicating a formation porosity distribution over the space spanned by $T_1$, $T_2$ and D.

12. The method according to claim 1, further comprising the step of characterizing uncertainty of a calculated optimal vector φ* indicating a formation porosity distribution by seeking an optimal vector φ** the distance of which to φ* is maximal whereby to provide a measure of confidence in the respective optimal solutions φ* and φ**.

13. The method according to claim 12, further comprising the steps of iteratively calculating plural optimal solution vectors $\{\varphi^{*(n)}\}_n$ and q) using the plural optimal solution vectors $\{\varphi^{*(n)}\}_n$ to provide one or more measures of confidence in any optimal solution vector.

14. The method according to claim 7, further comprising the step of characterizing uncertainty of a calculated optimal vector φ* indicating a formation porosity distribution by seeking an optimal vector φ** the distance of which to φ* is maximal whereby to provide a measure of confidence in the respective optimal solutions φ* and φ; and including the step r) of calculating φ using the expression $$\varphi^{**} = \underset{\varphi \in P}{\operatorname{argmax}} \|\varphi - \varphi^*\|_2^2$$

where P denotes the optimal solution space wherein any solution satisfies the domain constraints and admits an optimal objective value.

15. The method according to claim 14, further comprising the step of calculating $\{\varphi^{*(n)}\}_n$ using the expression $$\varphi^{*(n)} = \underset{\varphi \in P}{\operatorname{argmax}} \left\| \varphi - \left( \underset{\substack{\Sigma_{i=1}^{n-1} \alpha_i = 1 \\ \alpha_i \geq 0}}{\operatorname{argmin}} \left\| \varphi - \sum_{i=1}^{n-1} \alpha_i \varphi^{*(i)} \right\|_1 \right) (\varphi^{*(i)})_{i=1 \ldots n-1} \right\|_2^2$$

where P denotes the optimal solution space wherein any solution satisfies the domain constraints and admits an optimal objective value.

16. The method according to claim 1, further comprising the step of defining the boundaries of the solution space containing the one or more optimal solutions by determining one optimal vector $\varphi^{**}$ the distance of which from an optimal vector $\varphi^*$ is maximal, the method including iterating the determination of optimal maximally distant vectors $\{\varphi^{*(n)}\}_n$ defining the boundaries until the increase in the span of the collective set of determined optimal solutions with each iteration becomes less than a respective predetermined amount; labeling each optimal solution in the generated solution set defining the set of all boundaries to the solution space according to the fluid types present therein; and calculating the volume of each of the one or more fluid types in each of the enumerated optimal solutions defining the boundaries of the solution space.

17. The method according to claim 1, further comprising the step of defining the boundaries of the solution space containing the one or more optimal solutions by selecting, based on prior domain knowledge, one or more extreme solutions guaranteed to lie outside the solution space; and projecting the extreme solutions onto the solution space in order to define the boundaries of the space; labeling each optimal solution in the generated solution set defining the set of all boundaries to the solution space according to fluid types present therein; and calculating the volume of each of the one or more fluid types in each enumerated optimal solution collectively defining the boundaries of the solution space.

18. The method according to claim 1, further comprising the step of using the identified and volume-quantified optimal on-boundary solutions to characterize the volumetric distribution of each identified fluid.

19. An apparatus for evaluating for fluid in a fluid-containing formation intersected by a borehole, the apparatus comprising:
a Nuclear Magnetic Resonance (NMR) logging tool logging along the borehole in the fluid-containing formation, the NMR logging tool including one or more generators generating a static magnetic field emissive into the fluid-containing formation; one or more generators generating a sequence of magnetic pulses emissive into the fluid-containing formation; and one or more antennae detecting NMR signal values resulting from interaction between the emitted magnetic energy and protons in the fluid-containing formation and generating NMR log data therefrom; and one or more programmable devices in operable communication with the NMR logging tool, wherein the one or more programmable devices are programmed to:
invert a three-dimensional fluid property distribution of fluid in the fluid-containing formation from the NMR log data to image the NMR log data of the fluid-containing formation;
compare the detected NMR signal with a plurality of modeled signals ($\hat{y}$) derived from precomputed values of NMR signal contributions at points in a solution space spanned by longitudinal relaxation time $T_1$ transverse relaxation time $T_2$, and coefficient of molecular diffusion D;
identify one or more said modeled signals ($\hat{y}$) in respect of which an objective function o(y, $\hat{y}$) involving a respective detected NMR signal (y) and said modeled signal ($\hat{y}$) is optimised;
determine one or more optimal solution vectors $\varphi$ corresponding to the one or more optimised signal values ($\hat{y}$) at the aforesaid points in the solution space spanned by $T_1$, $T_2$ and D;
generate, from the determination, image information representative of one or more properties of the fluid in the fluid-containing formation; and
define boundaries of the solution space containing the one or more optimal solution vectors $\varphi$, and use said bounded solution space in a further step of fluid type identification and volume quantification with uncertainty analysis to assess the fluid in the formation from the image information.

20. The apparatus according to claim 19, wherein the programmable device is further programmed to use each said selected precomputed value to optimize an objective function involving one or more properties of fluid in the fluid-containing formation.

21. The apparatus according to claim 19, wherein the NMR logging tool is capable of storing one or more values of the detected NMR signals.

22. The apparatus according to claim 19, wherein the or at least one said programmable device is capable of storing one or more of the detected NMR signal.

23. The apparatus according to claim 19, wherein the one or more programmable devices are programmed to compute values of NMR signal contribution values at ($T_1$, $T_2$, D) value tuples using the three-dimensional kernel expression $$K_{[T_1, T_2, D]}(t) = K_{T_1}(t) K_{T_2}(t) K_D(t)$$

in which the value of each individual kernel at decay time t is given by $$K_{T_1}(t) = 1 - \exp\left(-\frac{WT_t}{T_1}\right)$$

$$K_{T_2}(t) = \exp\left(-\frac{t}{T_2}\right)$$

$$K_D(t) = \exp\left(-\frac{1}{12}\gamma^2 g^2 t_E^2 Dt\right)$$

wherein $\gamma$ is a fundamental property of the protons in the fluid in the borehole; g is the gradient of the static magnetic field; $t_E$ is the inter-echo time as defined herein; and $WT_t$ is the wait time for magnetization before the particular decay associated with time tick t occurs, said computing occurring before comparison of the stored echo signal values with a plurality of modeled signal values (ŷ) derived from precomputed values of NMR signal contributions at the value tuples of ($T_1$, $T_2$, D).

24. The apparatus according to claim 19, wherein the NMR logging tool is capable of storing the precomputed values of NMR signal contribution values at the ($T_1$, $T_2$, D) value tuples as a three-dimensional matrix.

25. The apparatus according to claim 19, wherein one or more said programmable devices is capable of storing the precomputed values of NMR signal contribution values at the ($T_1$, $T_2$, D) value tuples as a three-dimensional matrix.

26. The apparatus according to claim 19, wherein one or more said programmable devices is capable of identifying one or more said modeled signal values (ŷ) in respect of which a difference between a respective detected NMR echo signal (y) and said modeled signal (ŷ) is optimised by evaluating the expression $o(y, ŷ)=\|y-ŷ\|_1$ wherein (y) is the NMR signal detected by the NMR logging tool; and ŷ is the modeled counterpart signal derived from precomputed values of three-dimensional NMR signal contribution values at the ($T_1$, $T_2$, D) value tuples.

27. The apparatus according to claim 19, wherein one or more said programmable devices is programmed to use each said selected precomputed value to optimize an objective function involving one or more properties of fluid in the fluid-containing formation by using an equation of the form:

$$ŷ = k·φ$$

wherein k represents the contribution values at the ($T_1$, $T_2$, D) value tuples and φ represents a said property vector of the fluids in the fluid-containing formation.

28. The apparatus according to claim 19, wherein one or more said programmable devices is programmed to constrain the solution vector φ optimizing the objective function o(y, ŷ) according to:

$$φ_i \geq 0 \; \forall i$$

$$\Sigma_i φ_i \leq φ_{max}^\Sigma$$

$$|\Sigma_{\{i|i \text{ is even and } 1 \leq i \leq |φ^s|\}} φ_i^s - \Sigma_{\{i|i \text{ is odd and } 1 \leq i \leq |φ^s|\}} φ_i^s| \leq \tau \forall S.$$

29. The apparatus according to claim 19, wherein one or more said programmable devices is programmed to determine upper and lower bounds on any dimension or sum of dimensions of the vector φ residing in the set of optimal solutions for φ optimizing the objective function o(y, ŷ).

30. The apparatus according to claim 19, wherein one or more said programmable devices is programmed to determine upper and lower bounds on any dimension or sum of dimensions in any optimal solution for φ optimizing the objective function o(y, ŷ) and use the determined upper and lower bounds to characterize the uncertainty in a calculated optimal solution for φ indicating a formation porosity distribution over the space spanned by $T_1$, $T_2$ and D.

31. The apparatus according to claim 19, wherein one or more said programmable devices is programmed to carry out the step of characterizing uncertainty of a calculated optimal vector φ* indicating a formation porosity distribution by seeking an optimal vector φ** the distance of which to φ* is maximal whereby to provide a measure of confidence in the respective optimal solutions φ* and φ**.

32. The apparatus according to claim 19, wherein one or more said programmable devices is programmed to calculate φ using the expression $$φ^{} = \underset{φ \in P}{\arg\max} \|φ - φ^*\|_2^2$$

where P denotes the solution space wherein any solution satisfies the domain constraints and admits an optimal objective value.

33. The apparatus according to claim 32, wherein one or more said programmable devices is programmed iteratively to calculate plural optimal solution vectors $\{φ^{*(n)}\}_n$ and use the plural optimal solution vectors to provide one or more measures of confidence in any optimal solution vector.

34. The apparatus according to claim 19, wherein one or more said programmable devices is programmed to define the boundaries of the solution space containing the one or more optimal solutions by determining one optimal vector φ** the distance of which from an optimal vector φ* is maximal, by iterating the determination of optimal maximally distant vectors $\{φ^{*(n)}\}_n$ until the increase in the span of the collective set of determined optimal solutions with each iteration becomes less than a respective predetermined amount; by labeling each optimal solution in the generated solution set defining the set of all boundaries to the solution space according to fluid types present therein; and by calculating the volume of each of the one or more fluid types in each enumerated optimal solution defining the boundaries of the solution space.

35. The apparatus according to claim 19, wherein one or more said programmable devices is programmed to define the boundaries of the solution space containing the one or more optimal solutions by selecting, based on prior domain knowledge, one or more extreme solutions guaranteed to lie outside the solution space; by projecting the extreme solutions onto the solution space in order to define the boundaries of the space; by labeling each optimal solution in the generated solution set defining the set of all boundaries to the solution space according to fluid types present therein; and by calculating the volume of each of the one or more fluid types in each enumerated optimal solution collectively defining the boundaries of the solution space.

36. The apparatus according to claim 19, wherein one or more said programmable devices is programmed to use the identified and volume-quantified optimal on-boundary solutions to characterize the volumetric distribution of each labeled fluid.

37. The apparatus according to claim 19, further comprising one or more displays for displaying the image information as graphical, image log, tabular or digital information representative of the one or more properties of the fluid in the fluid-containing formation.

\* \* \* \* \*